United States Patent
Amarasinghe

(10) Patent No.: US 8,505,538 B2
(45) Date of Patent: *Aug. 13, 2013

(54) HEADGEAR

(75) Inventor: Amal Shirley Amarasinghe, Beecroft (AU)

(73) Assignee: Resmed Limited, Bella Vista (AU)

(*) Notice: Subject to any disclaimer, the term of this patent is extended or adjusted under 35 U.S.C. 154(b) by 0 days.

This patent is subject to a terminal disclaimer.

(21) Appl. No.: 12/805,787

(22) Filed: Aug. 19, 2010

(65) Prior Publication Data
US 2010/0319688 A1 Dec. 23, 2010

Related U.S. Application Data

(60) Division of application No. 11/701,362, filed on Feb. 2, 2007, now Pat. No. 7,802,573, which is a continuation of application No. 10/433,799, filed as application No. PCT/AU01/01607 on Dec. 12, 2001, now Pat. No. 7,188,620.

(60) Provisional application No. 60/254,537, filed on Dec. 12, 2000.

(51) Int. Cl.
*A62B 18/08* (2006.01)
*A62B 18/02* (2006.01)

(52) U.S. Cl.
USPC .................. 128/207.11; 128/206.21

(58) Field of Classification Search
USPC 128/200.24, 201.22–201.24, 201.27–201.29, 128/202.11, 202.27, 203.29, 205.25, 206.12, 128/206.14, 206.18, 206.21, 206.24, 848, 128/207.11–207.13, 207.17
See application file for complete search history.

(56) References Cited

U.S. PATENT DOCUMENTS

| | | | |
|---|---|---|---|
| RE20,211 E | | 12/1936 | Motsinger |
| 4,099,524 A | * | 7/1978 | Cueman et al. ................. 602/19 |
| 4,367,735 A | | 1/1983 | Dali et al. |
| 4,437,462 A | | 3/1984 | Piljay et al. |
| 4,640,269 A | * | 2/1987 | Goins ............................ 602/19 |
| 5,117,819 A | | 6/1992 | Servidio et al. |
| D334,633 S | | 4/1993 | Rudolph |

(Continued)

FOREIGN PATENT DOCUMENTS

| | | |
|---|---|---|
| EP | 0 747 078 A2 | 12/1996 |
| EP | 1 020 201 A2 | 7/2000 |

(Continued)

OTHER PUBLICATIONS

Supplementary European Search Report for EP 01270356.7 mailed Feb. 3, 2006, 3 pages.

(Continued)

*Primary Examiner* — Justine Yu
*Assistant Examiner* — Rachel Young
(74) *Attorney, Agent, or Firm* — Nixon & Vanderhye, P.C.

(57) ABSTRACT

A headgear for securing and positioning a mask suitable for the treatment of sleep disordered breathing is constructed from a composite including polyurethane foam. It includes a back portion with upper and lower straps connected to the back portion. The straps have relatively narrow strap ends the lower straps are displaced downward with respect to the back portion. A quick release mechanism near the front of the face attaches the headgear to the mask. Additional components can be attached to the straps to alter their elasticity and stiffness.

73 Claims, 5 Drawing Sheets

(56) References Cited

U.S. PATENT DOCUMENTS

| | | | |
|---|---|---|---|
| 5,284,469 | A | 2/1994 | Jasen et al. |
| 5,481,763 | A | 1/1996 | Brostrom et al. |
| 5,488,948 | A | 2/1996 | Dubruille et al. |
| 5,490,504 | A | 2/1996 | Vrona et al. |
| 5,517,986 | A | 5/1996 | Starr et al. |
| 5,529,062 | A | 6/1996 | Byrd et al. |
| 5,542,128 | A | 8/1996 | Lomas et al. |
| 5,560,354 | A * | 10/1996 | Berthon-Jones et al. 128/205.25 |
| D383,204 | S | 9/1997 | Lomas |
| 5,806,516 | A * | 9/1998 | Beattie ............... 128/207.17 |
| 5,840,050 | A * | 11/1998 | Lerman ............... 602/19 |
| 5,921,239 | A * | 7/1999 | McCall et al. ........ 128/205.25 |
| 5,924,421 | A | 7/1999 | Rosbrook et al. |
| 5,950,248 | A | 9/1999 | Kawashima et al. |
| 6,016,807 | A | 1/2000 | Lodge |
| 6,062,222 | A | 5/2000 | Lewis et al. |
| 6,105,573 | A | 8/2000 | Delaplane et al. |
| 6,119,693 | A | 9/2000 | Kwok et al. |
| D433,127 | S | 10/2000 | Gazzara |
| 6,269,814 | B1 | 8/2001 | Blaszczykiewicz et al. |
| 6,422,238 | B1 | 7/2002 | Lithgow |
| 6,470,886 | B1 * | 10/2002 | Jestrabek-Hart ......... 128/207.11 |
| 6,494,207 | B1 | 12/2002 | Kwok |
| 6,591,837 | B1 * | 7/2003 | Byram ............... 128/206.24 |
| 6,732,733 | B1 * | 5/2004 | Brostrom et al. ........ 128/206.27 |
| 6,772,760 | B2 | 8/2004 | Frater et al. |
| 7,188,620 | B2 | 3/2007 | Amarasinghe |
| 7,219,669 | B1 * | 5/2007 | Lovell et al. ............. 128/206.24 |
| 2004/0067333 | A1 | 4/2004 | Amarasinghe |
| 2004/0112377 | A1 | 6/2004 | Amarasinghe et al. |
| 2007/0169777 | A1 | 7/2007 | Amarasinghe |

FOREIGN PATENT DOCUMENTS

| | | |
|---|---|---|
| EP | 1 057 494 A2 | 12/2000 |
| FR | 2 618 340 A | 1/1989 |
| GB | 2 247 396 A | 3/1992 |
| WO | WO 96/25983 | 8/1996 |
| WO | WO 96/28207 | 9/1996 |
| WO | 98/48878 A2 | 11/1998 |

OTHER PUBLICATIONS

European Office Action for corresponding EP Application No. 01 270 356.7, mailed Jun. 11, 2007, 3 pages.
U.S. Appl. No. 60/293,992, filed May 30, 2001, Frater et al.
U.S. Appl. No. 60/219,618, filed Jul. 21, 2000, Frater et al.
U.S. Appl. No. 60/213,251, filed Jun. 22, 2000, Frater et al.
Extended European Search Report in EP 10 18 5039 dated Feb. 16, 2011.
Extended European Search Report in EP 10 18 5034 dated Feb. 22, 2011 (6 pages).
European Search Report for corresponding EP Appln No. 10183627, mailed Mar. 17, 2011, 12 pages.
European communication corresponding EP Appln No. 10 183 527.8-1662, mailed Jun. 13, 2013, 3 pages.

* cited by examiner

HEADGEAR

CROSS-REFERENCES TO RELATED APPLICATIONS

This is a division of U.S. application Ser. No. 11/701,362, filed Feb. 2, 2007, allowed, which is a continuation of U.S. application Ser. No. 10/433,779, filed Jun. 6, 2003, now U.S. Pat. No. 7,188,620, which is a national phase of International Application No. PCT/AU01/01607, filed Dec. 12, 2001, which claims the benefit of U.S. Provisional Application No. 60/254,537, filed Dec. 12, 2000, each incorporated herein by reference in its entirety.

BACKGROUND OF THE INVENTION

1. Field of the Invention

The invention relates to headgear for use with a mask suitable for the delivery of non-invasive positive pressure ventilation and for nasal CPAP treatment of sleep disordered breathing conditions such as obstructive sleep apnea.

2. Description of Related Art

Obstructive Sleep Apnea (OSA) is a disease characterised by excessive daytime sleepiness, loud snoring and daytime irritability. Other effects of OSA can include depression, high blood pressure, serious heart conditions, sexual problems, memory lapses, intellectual deterioration and morning headaches.

The treatment of OSA by the application of nasal Continuous Positive Airway Pressure (CPAP) was invented by Sullivan and is described in U.S. Pat. No. 4,944,310 (Sullivan, assigned to ResMed Limited). The technique involves the application of a flow of pressurised breathable gas (typically room air) to either the nose or nose and mouth of a patient while they sleep. The technique is said to "splint" open the airways. Typical treatment pressures are in the range of 3 to 20 cm H2O. Flows are up to approximately 200 L/min. The flow of pressurised air is produced by a blower and delivered to the patient via a patient interface. The blower and patient interface are joined by a conduit. Whilst there are other techniques for the treatment of OSA, such as surgery, the use of CPAP has become the "gold" standard.

For a particular patient, the pressure which is needed to maintain open airways can vary throughout the night and vary on different nights. U.S. Pat. No. 5,245,995 (Sullivan and Lynch, assigned to ResMed Limited) describes a method and device for varying the pressure in accordance with indications. For example, if the patient starts to snore, the pressure automatically increases, whilst in the absence of snoring, the pressure automatically decreases.

Non-Invasive Positive Pressure Ventilation (NIPPV) is another form of treatment for breathing disorders. In its most basic form, it involves a relatively higher pressure of gas being provided in the patient mask during the inspiratory phase of respiration and a relatively lower pressure or atmospheric pressure being provided in the patient mask during the expiratory phase of respiration. Typical treatment pressures are in the range of 3 to 30 cmH, 0.

In other NIPPV modes, the pressure can be made to vary in a complex manner throughout the respiratory cycle. For example, the pressure at the mask during inspiration or expiration can be varied through the period of treatment, as disclosed in international PCT patent application no. PCT/AU97/00631(Berthon-Jones, assigned to ResMed Limited).

In this specification, any reference to CPAP is to be understood as embracing all of the above-described forms of ventilatory treatment or assistance.

One of the earliest patient interfaces for providing CPAP treatment was constructed to include a fibreglass model of the patient's nose. The model was adhered to the patient's nose each night and removed each morning. An advantage of this patient interface included the customised fit, which assisted in a good seal between the patient interface and the patient's airways. However, the use of adhesive to secure the mask was inconvenient and not desirable.

Another suitable patient interface is described in U.S. Pat. No. 5,243,971 (Sullivan and Bruderer, assigned to the University of Sydney), entitled "Nasal Mask for CPAP having Ballooning/Moulding Seal with Wearer's Nose and Facial Contours". This patent describes a nasal mask with a soft face-contacting portion, and a rigid shell. The mask is held in position using headgear. The headgear is attached to the mask and passes around the back of the wearer's head. The patent depicts two sets of straps in the headgear. The first set comprised a pair of straps passing from the forehead region to the back of the head. The second set comprised a pair of straps passing from the nasal region of the mask to the back of the head.

Another known patient interface is the MIRAGE® nasal mask (by ResMed Ltd). This nasal mask includes a pair of headgear attachment points in the nasal region of the mask shell and a forehead support that includes another pair of headgear attachment points. The headgear includes a single piece of a soft, flexible composite fabric with a generally triangular back portion and four straps. The four straps include a pair of upper straps and a pair of lower straps connecting to the headgear attachment points on the forehead support and nasal mask shell respectively. At the end of each strap is secured a piece of hook material, which, in use, passes through a headgear attachment point and fastens on corresponding loop material on the strap. The generally triangular back portion engages the skull in the region of the occiput. The fabric stretches under a load. The base of the triangle is positioned near and generally in line with the upper straps. Each strap is approximately 2 cm wide and approximately 3 mm thick. The fabric is a composite of three layers. The inner layer, closest to the patient's head, is made from nylon. The middle layer is made from neoprene. The outer layer is made from loop material, suitable for engaging with hook fastening material such as Velcro™. The upper straps have an approximate length of 19 cm, from the end to the closest corner of the triangle, whilst the lower straps have an approximate length of 26 cm. Including the triangle, the upper and lower straps each have an approximate total length of 60.5 cm. The triangular back portion is an approximate isosceles triangle, with a base of approximately 13.5 cm and sides of approximately 9 cm.

Some patients open their mouths during sleep, which means that they may not receive the benefit of CPAP due to mouth leaks. Various solutions have been proposed for this problem. One solution is taught in U.S. Pat. No. 6,123,082 (Berthon-Jones, assigned to ResMed Limited), whereby the lips are held closed. Another solution is to use a mask that covers both the nose and mouth of the patient. An example of a mouth and nasal mask is described in U.S. Pat. No. 5,560,354 (Berthon-Jones, Calluaud, Lynch & Hely, assigned to ResMed Limited).

Another suitable mask system is the MIRAGE® full-face mask (by assignee ResMed Limited). The MIRAGE® full-face mask and headgear is illustrated in FIGS. 1, 2 and 3. Suitable headgear (102) for this mask (100) is constructed from a composite material of nylon, neoprene and loop material. The headgear similarly comprises a pair of upper (104) and a pair of lower straps (106) and a generally triangular back portion (108). The upper strap has a total length of approximately 610 mm as shown in FIG. 3. The straps have an approximate width of 25 mm, however, the upper strap has an approximate width of 19 mm. The triangular region has a base of approximately 15.5 cm and two equal sides of approximately 11 cm. The upper and lower straps are approximately 192 mm apart. In addition, the headgear includes a quick release mechanism (110), as described in the pending U.S. patent application Ser. No. 09/482, 718 (Lithgow, assigned to ResMed Limited). The quick release mechanism provides a "rip-chord" that can be pulled upon to separate the headgear and remove the mask in an emergency. When the headgear is positioned on the patient's head, the quick-release mechanism is situated at the back of the head and the chord runs through loops towards the front of the mask system.

Patient interface arrangements include nasal masks, nose and mouth masks, nasal prongs and nasal pillows. In all forms of patient interface used with CPAP for treating sleep disordered breathing, there is a need to counterbalance the force of the pressurised air and to correctly position the interface. Since the patient must sleep with this interface, it is important that it be comfortable. From the manufacturing and distribution channel perspectives, it is advantageous if one size of headgear fits a large range of head shapes and sizes.

It should be noted that while there are many mask and headgear arrangements available for ventilators, respirators, aviator masks and other breathing apparatus, in general, these may not be suitable for use in the treatment of sleep disordered breathing because they are not sufficiently comfortable to allow the patient to sleep.

The present invention is directed towards providing headgear for holding and securing a mask for use in the treatment of sleep disordered breathing which improves patient comfort, is long lasting and fits a wide range of head shapes and sizes.

BRIEF SUMMARY OF THE INVENTION

The invention provides headgear for securing and positioning a mask suitable for the treatment of sleep disordered breathing with the following advantageous combination of features:
(i) Constructed from a composite including polyurethane foam
(ii) Relatively narrow strap ends,
(iii) Displaced lower strap,
(iv) A quick release mechanism near the front of the face; and
(v) Additional attached components to alter the elasticity and stiffness of the straps.

DETAILED DESCRIPTION OF THE INVENTION

Figure 1:
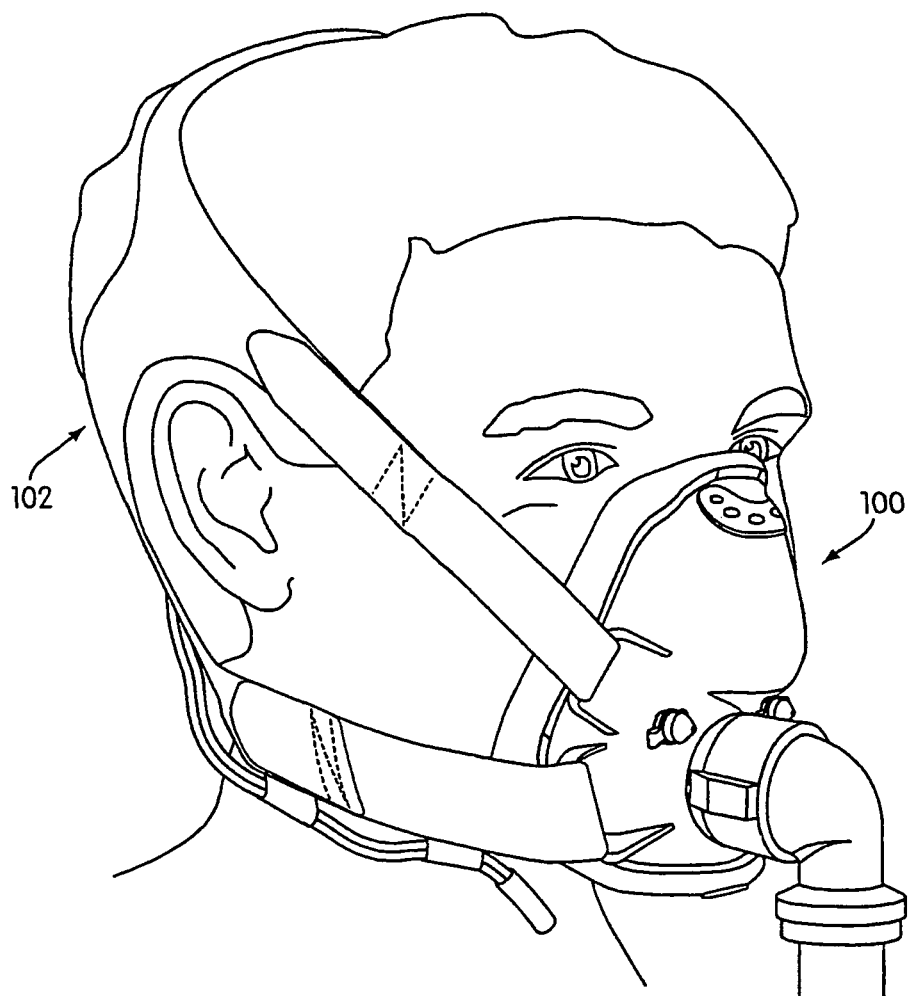
FIG. 1 shows a front three-quarter view of a MIRAGE® full-face mask and prior art headgear system in position on a patient's head.
Figure 2:
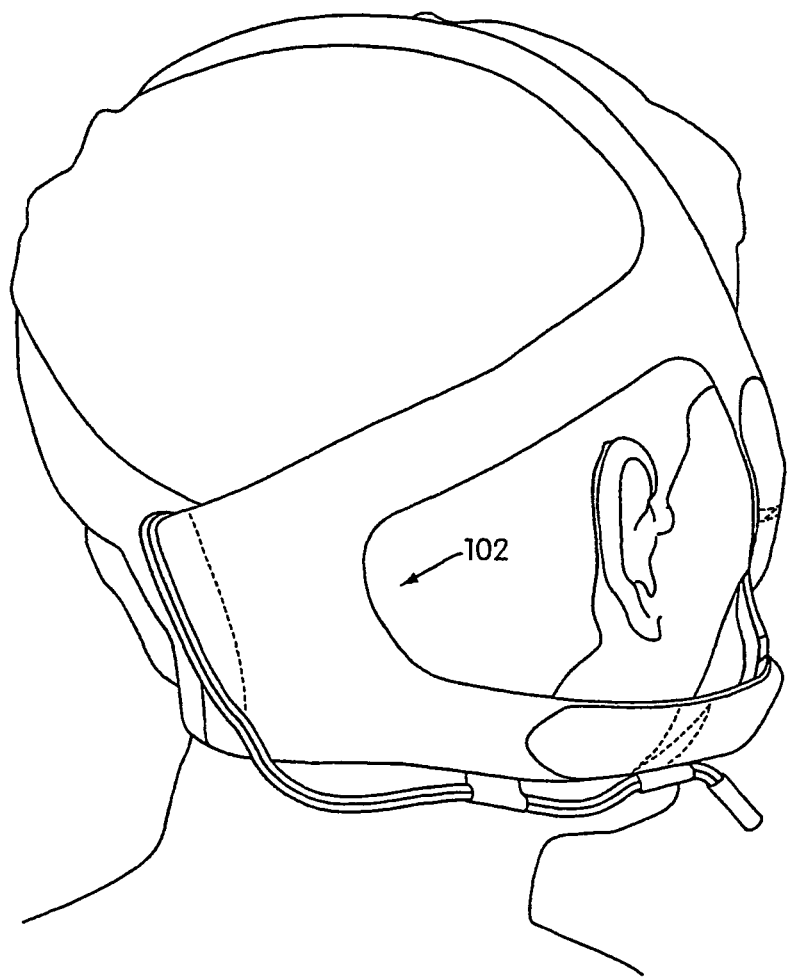
FIG. 2 shows a rear three-quarter view of a MIRAGE® full-face mask and prior art headgear system on a patient's head.
Figure 3:
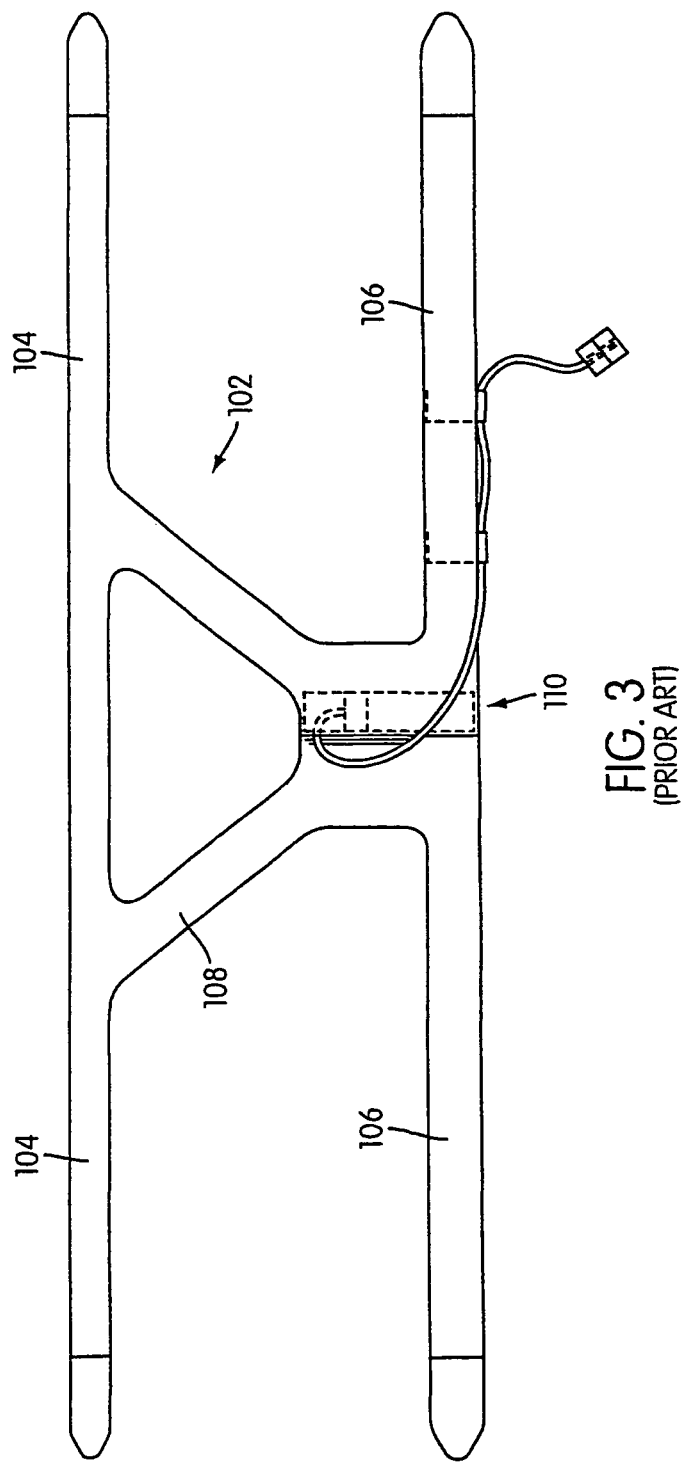
FIG. 3 shows a view of prior art full-face mask headgear laid flat.

The invention provides headgear (10) for securing and positioning a mask suitable for the treatment of sleep disordered breathing.
(i) Material The headgear is constructed from a composite of polyurethane foam, loop material and hook material whose shape includes a pair of upper straps (20) and lower straps (30) and a generally triangular back portion (40). A piece of hook material (22) is attached to the end of each of the four straps so that the straps may be secured to the attachment points on the mask. The end includes a main body (23) and a tapered free end portion (25).

The composite has three layers. The first layer, which in use is positioned against the head of the patient, is constructed from polyester or nylon fabric. The second, middle layer is constructed from an hypoallergenic breathable polyurethane foam. The third layer is constructed from loop material. A suitable material for constructing the composite is BREATH-O-PRENE® manufactured by ACCUMED, New York, United States of America. The total thickness of the composite is approximately 2 mm. The upper and lower pairs of straps are approximately 150 mm apart when laid flat. The upper and lower straps have an approximate total length (from the left side to the right side) of 610 mm.

The generally triangular back portion (40) of the headgear (10) is constructed and arranged to engage generally with the occiput of the patient's head in use. In use, the base of the triangle is positioned at the crown of the head, while the apex of the triangle lies generally just above the point of contact between the skull and the muscles of the neck.
(ii) Relatively Narrow Strap Ends The headgear of the present invention is configured to minimize the discomfort associated with the use of hook material. In prior art headgear, that discomfort can arise where the hook material may be in contact with the patient's skin, say the cheek or neck regions, for extended periods of time. That undesirable contact will occur where the hook material, to some extent is not entirely located on the receiving loop material, but lies tangential to the loop material, and to some extent extends beyond the loop material and comes in contact with the patient's skin, either continuously while the headgear is in use or when it is compressed against the skin, as can occur when the patient head changes position during the sleep period.

Figure 4:
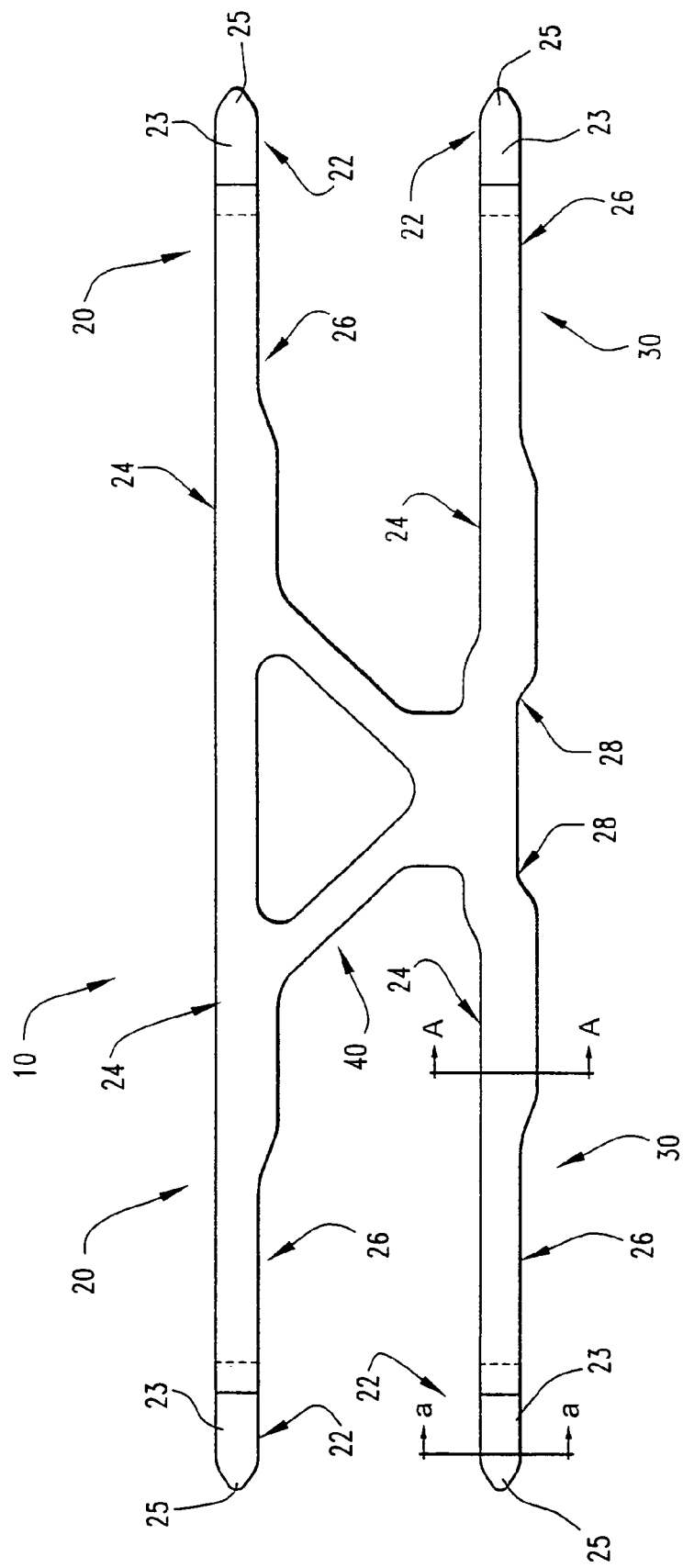
FIG. 4 shows a view of headgear according to an embodiment of the present invention.

As shown in FIG. 4, the width of each lower strap is constant for approximately half their length, forming a relatively wide portion (24), and then over a relatively short distance, changes to a narrower width for the remaining half of their length, forming a relatively narrow portion (26), terminating at the point where the hook material (22) is joined to the composite material. A characteristic of this configuration is that the point of contact where the hook material detachably binds with the strap loop material is positioned on the wide portion (24) and is wider by approximately 1 cm than the width of the engaging hook material. By adopting this configuration, the target region for binding is relatively greater in area than is the case with prior art. Prior art headgear includes a tapered end hook section that is of narrower width than that of the intended contact loop section of the strap. However, the prior art hook section tapered end is less than one half the length of the hook section, that is, it does not represent the majority of the length of the hook section nor does its length represent the majority of the length of the intended corresponding contact loop section (i.e., the maximum extent of the loop section covered by the hook section).

In contrast to the prior art, with the present invention the attachment of the hook material is facilitated, as relatively less precision is required in the placement of the hook section to achieve binding. This reduced dependence on precision is of advantage to all persons using the headgear and is of particular benefit to the user that may be trying to fit the headgear in a home environment and where it is not possible to directly sight the headgear components they are manipulating. Furthermore, compared to the prior art (where the hook material and the target region are of substantially the same width), this configuration reduces the chance of exposing some of the hook material to interfere with the wearer, causing discomfort and possibly skin irritation or abrasion.

(iii) Displaced Lower Strap

A length of each of the left and right lower straps is displaced vertically lower by approximately 1 cm (28). By adopting this configuration, it is possible to optimize the design of the base of the back portion so as to achieve the desired security of attachment but avoid compromising comfort in a situation where the lowest point of the headgear in the occiput region is extended to a position that is lower than is otherwise required in order to achieve a sufficiently lowest strap point. This approach avoids the prior art problem of having the headgear rear portion extending beyond what would otherwise be required and thereby engaging the sensitive area below the occipital lobe.

(iv) Quick Release Mechanism

Figure 5:
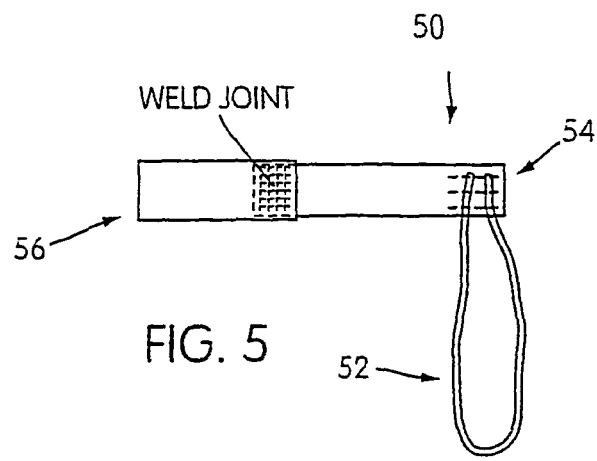
FIG. 5 shows a view of the quick release mechanism according to the present invention.

Preferably the headgear of the present invention includes a quick release mechanism (50) (see FIG. 5), and this is especially so when the headgear is intended to be used with a mask that covers the patient's nose and mouth.

The quick-release mechanism (50) suitable for incorporation into the preferred embodiment is constructed from a sub-assembly of three components: (i) a release loop of a cord material (52), (ii) a generally rectangular length of hook material (54), and (iii) a generally rectangular length of a composite fabric (56) which can bind to the hook material, as discussed above. The sub-assembly is generally rectangular in shape and in use forms an extension of one of the lower straps. Preferably the loop cord is constructed from braided cord about 17 cm long. The cord loop (52) is sewn to one end of the length of hook material (54). The hook material (54) and composite fabric (56) are joined at the other end of the hook material (54), preferably via a weld joint. In use, the end of the hook material (54), to which is connected the loop cord (52), is secured, using the hook and loop mechanism, to the end of a modified lower strap which, in contrast to the lower straps (30) shown in FIG. 4, does not contain hook material. The other end (56) of the quick release mechanism (50) is free to be connected to a headgear attachment point on the mask shell and releasably attached to an exposed portion of the hook material (54). If it is desired to use the quick-release mechanism (50), it is convenient for the patient to pull down on the loop of braided cord (52), thereby disengaging the lower strap from the mask shell and allowing the mask to then be readily removed from the patient's face. A quick-release mechanism of this configuration may be used on headgear that is fabricated of materials and in configurations that are different to those of the type described above and as such is an invention in its own right.

(v) Altering the Stiffness and Extensibility

Figure 6A:
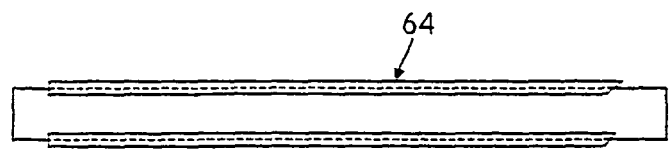
FIG. 6 shows a view of mask headgear straps in accordance with the present invention laid flat.
Figure 6B:

In one form of the invention, the extensibility of the straps can be altered by attaching lengths of generally inextensible material (62) such as cotton or silk to the straps, as shown in FIG. 6b. The effect of this arrangement is to make the headgear less extensible along the length of the straps than in a vertical direction. In a preferred embodiment, lengths of cotton are sewn to the straps.

In another form of the invention, the stiffness of the straps can be altered by attaching stiffening material (64) to the top and bottom edge of the straps, as shown in FIG. 6a. Alternatively, or in addition, the strap may be stiffened by any other suitable means including by adding stitching as lines, in a crisscross pattern, or both. This makes the headgear less "floppy" and more convenient to put on the head of a wearer.

In another form of the invention, the headgear is constructed from an anisotropic material that is more extensible in a first direction than in a direction at an angle of 90 degrees to the first direction. This enables the headgear to be cut from a single piece of composite material and yet have different extensibilities in different directions. Preferably, the headgear will be more extensible in a vertical direction than in a horizontal direction. Hence the upper and lower straps will be less extensible in a direction along their length than in a direction along their width. This means that the back portion of the headgear can be more extensible in a direction from the base of the skull to the crown, than in a direction at right angles to that direction.

The invention claimed is:

1. A headgear for securing and positioning a mask suitable for the treatment of a patient suffering from sleep disordered breathing, comprising:

a back portion, the back portion including a top portion, a bottom portion, and a pair of side portions, the pair of side portions converging towards one another as the pair of side portions extend between the top portion and the bottom portion;

a pair of elongated upper straps extending from the back portion on opposing sides of the back portion and extending away from the back portion, each of the upper straps having a first portion with a loop material portion between the back portion and a second portion, the second portion including a hook material portion at a free end for attaching the mask;

a pair of elongated lower straps extending from the back portion below the upper straps on opposing sides of the back portion and extending away from the back portion, each of the lower straps having a first portion with a loop material portion between the back portion and a second portion, the second portion including a hook material portion at a free end for attaching the mask; and a transition between the back portion and the lower straps, the transition having a downwardly angled portion such that a lower edge of the lower straps is positioned lower than a lower edge of the bottom portion of the back portion in use.

2. The headgear of claim 1, wherein the upper straps and the lower straps consist essentially of four straps.

3. The headgear of claim 2, wherein a width of the upper straps and the lower straps along the loop portion to which the hook portion releasably attaches is wider than the hook portion, and wherein a maximum width of the hook portion is less than a width of the loop portion where they attach to one another.

4. The headgear of claim 3, wherein the loop portion to which the hook portion releasably attaches is wider than at least part of the hook portion by approximately 1 cm.

5. The headgear of claim 3, wherein the pair of upper straps are substantially parallel to the pair of lower straps.

6. The headgear of claim 5, wherein the pair of upper straps are dimensioned to be positioned above a patient's ears and the pair of lower straps are dimensioned to be positioned below a patient's ears.

7. The headgear of claim 6, wherein the headgear is formed of a composite having a first layer, adapted to be positioned against a head of the patient, constructed from a polyester or nylon fabric, a second, middle layer constructed from a polyurethane foam and a third layer constructed from loop material adapted to engage and attach to a hook material.

8. The headgear of claim 7, wherein each of the lower straps includes an upwardly angled portion, the upwardly angled portion having a lower edge that angles upward relative to the lower edge of the bottom portion of the back portion.

9. The headgear of claim 8, wherein, for each said lower strap, a first width of the loop portion oriented towards a main body of the hook portion on each of the straps is less than a second width of the loop portion oriented towards the back portion.

10. The headgear of claim 9, wherein a distance between the pair of upper straps and the pair of lower straps is approximately 150 mm.

11. The headgear of claim 10, wherein a length of the pair of upper straps and the pair of lower straps is approximately 610 mm.

12. A mask, comprising:
a frame supporting a soft face-contacting portion, the frame having a first pair of attachment points and a second pair of attachment points; and
the headgear of claim 1, wherein the pair of upper straps is adapted to be coupled to the first pair of attachment points and the pair of lower straps is adapted to be coupled to the second pair of attachment points.

13. The mask of claim 12, further comprising vent holes adapted to vent exhaled air from the mask.

14. The mask of claim 13, further comprising at least one port to communicate with an interior of the mask.

15. The mask of claim 14, further comprising an elbow connected to the frame, the elbow adapted to deliver pressurized gas to an interior of the mask.

16. The mask of claim 12, wherein the mask is a full face mask.

17. The mask of claim 12, wherein the mask is a nasal mask.

18. A headgear for securing and positioning a mask suitable for the treatment of a patient suffering from sleep disordered breathing, comprising:
a back portion having an opening; and
a pair of elongated upper straps connected to the back portion on opposing sides of the back portion and extending away from the back portion, each upper strap having a loop portion positioned along an external surface of its length and a hook portion at a free end thereof for releasably attaching to the loop portion to attach the pair of upper straps to the mask;
a pair of elongated lower straps connected to the back portion on opposing sides of the back portion and extending away from the back portion, each lower strap having a loop portion positioned along an external surface of its length and a hook portion at a free end thereof for releasably attaching to the loop portion to attach the pair of lower straps to the mask; and
a transition between the back portion and the lower straps, the transition having a downwardly angled portion such that a lower edge of the lower straps is positioned lower than a lower edge of the back portion in use,
wherein a width of the pair of upper straps and the pair of lower straps along the loop portion to which the hook portion releasably attaches is sufficiently wider than a maximum width of the hook portion such that when the hook portion is attached to the loop portion the strap shields the patient's face from contact with the hook portion, and
wherein a width of the loop portion varies along a length of the lower straps.

19. The headgear of claim 18, wherein the upper straps and the lower straps consist essentially of four straps.

20. The headgear of claim 19, wherein the upper straps and the lower straps are substantially parallel to each other.

21. The headgear of claim 20, wherein the pair of upper straps are dimensioned to be positioned above a patient's ears, and the pair of lower straps are dimensioned to be positioned below a patient's ears.

22. The headgear of claim 21, wherein the headgear is formed of a composite having a first layer, adapted to be positioned against a head of the patient, constructed from a polyester or nylon fabric, a second, middle layer constructed from a polyurethane foam and a third layer constructed from loop material adapted to engage and attach to a hook material.

23. The headgear of claim 22, wherein each of the lower straps includes an upwardly angled portion, the upwardly angled portion having a lower edge that angles upward relative to the lower edge of the back portion.

24. The headgear of claim 23, wherein, for each said lower strap, a first width of the loop portion oriented towards a main body of the hook portion on each of the straps is less than a second width of the loop portion oriented towards the back portion.

25. The headgear of claim 24, wherein a distance between the pair of upper straps and the pair of lower straps is approximately 150 mm.

26. The headgear of claim 25, wherein a length of the pair of upper straps and the pair of lower straps is approximately 610 mm.

27. A mask, comprising:
a frame supporting a soft face-contacting portion, the frame having a first pair of attachment points and a second pair of attachment points; and
the headgear of claim 18, wherein the pair of upper straps are adapted to be coupled to the first pair of attachment points and the pair of lower straps are adapted to be coupled to the second pair of attachment points.

28. The mask of claim 27, further comprising vent holes adapted to vent exhaled air from the mask.

29. The mask of claim 28, further comprising at least one port to communicate with an interior of the mask.

30. The mask of claim 29, further comprising an elbow connected to the frame, the elbow adapted to deliver pressurized gas to an interior of the mask.

31. The mask of claim 27, wherein the mask is a full face mask.

32. The mask of claim 27, wherein the mask is a nasal mask.

33. A headgear for securing and positioning a mask suitable for the treatment of a patient suffering from sleep disordered breathing, comprising:
a back portion, the back portion having a top portion and a bottom portion, the top portion arranged to engage with a crown of a patient's head, extending from a first lateral side to a second lateral side of the patient's head;
a pair of elongated upper straps provided to the back portion on opposing sides of the back portion and extending away from the back portion, each upper strap having a loop portion positioned along an external surface of its length and a hook portion at a free end thereof for releasably attaching to the loop portion to attach the upper straps to the mask; and a pair of elongated lower straps extending away from the back portion, each lower strap having a loop portion positioned along an external surface of its length and a hook portion at a free end thereof for releasably attaching to the loop portion to attach the lower straps to the mask, the lower straps being arranged so that the back portion is raised relative to at least a portion of the lower straps in use;

wherein each of the pair of upper straps and the pair of lower straps is formed of a composite having a first layer adapted to be positioned against the patient's head, a second, middle layer constructed from foam, and a third layer including said loop portion, and a width of each of the pair of upper straps and the pair of lower straps along the loop portion to which the hook portion releasably attaches is sufficiently wider than the hook portion such that when the hook portion is attached to the loop portion the strap tends to shield the patient's face from contact with the hook portion if the hook portion is slightly misaligned with the loop portion.

34. The headgear of claim 33, wherein the upper straps and the lower straps consist essentially of four straps.

35. The headgear of claim 34, wherein the pair of upper straps are structured and configured to extend above a patient's ears.

36. The headgear of claim 35, wherein the pair of lower straps are structured and configured to extend below a patient's ears.

37. The headgear of claim 36, wherein the pair of upper straps are arranged to be substantially parallel to each other.

38. The headgear of claim 37, wherein a thickness of the pair of upper straps and the pair of lower straps is approximately 2 mm.

39. The headgear of claim 38, wherein at least a portion of the pair of lower straps are arranged to be substantially parallel to each other.

40. The headgear of claim 39, wherein a width of the loop portion varies along a length of the pair of lower straps.

41. A mask, comprising:
a frame supporting a soft face-contacting portion, the frame having attachment points; and
the headgear of claim 33, wherein the upper straps and the lower straps are adapted to be coupled to the attachment points.

42. The mask of claim 41, further comprising vent holes adapted to vent exhaled air from the mask.

43. The mask of claim 42, further comprising at least one port in communication with an interior of the mask.

44. The mask of claim 43, further comprising an elbow connected to the frame, the elbow adapted to deliver pressurized gas to an interior of the mask.

45. The mask of claim 41, wherein the mask is a full face mask.

46. The mask of claim 41, wherein the mask is a nasal mask.

47. A mask assembly suitable for the treatment of sleep disordered breathing, comprising:
a mask to provide pressurized air to a patient, said mask having upper and lower slot features on each side of the mask;
a headgear assembly, comprising:
a back portion, the back portion having a top portion, a bottom portion and side portions, the side portions converging towards one another as the side portions extend between the top portion and the bottom portion;

a pair of elongated upper straps provided to the back portion on opposing sides of the back portion and extending away from the back portion, each upper strap having a loop portion positioned along an external surface of its length and a hook portion at a free end thereof for releasably attaching to the loop portion to attach the upper straps to the mask, wherein the pair of upper straps are dimensioned to extend above the patient's ears; and a pair of elongated lower straps extending away from the back portion, each lower strap having a loop portion positioned along an external surface of its length and a hook portion at a free end thereof for releasably attaching to the loop portion to attach the lower straps to the mask, the lower straps being arranged so that the back portion is raised relative to at least a portion of the lower straps in use, wherein the pair of lower straps are dimensioned to extend below the patient's ears and across the patient's cheeks, wherein an increased width portion of each of the pair of upper straps and the pair of lower straps along the loop portion to which the hook portion releasably attaches is wider than the hook portion, wherein each loop portion of each of the lower straps is configured to be retained on the mask assembly by passing through a respective slot feature and doubleback on itself to attach the headgear, wherein each increased width portion of each lower strap that engages with its respective hook portion is adapted to engage the patient's cheeks.

48. The mask assembly of claim 47, wherein the upper straps and the lower straps consist essentially of four straps.

49. The mask assembly of claim 47, wherein a width of the loop portion varies along a length of the pair of lower straps.

50. The mask assembly of claim 47, wherein the top portion of the back portion includes a top strap adapted to engage a crown of the patient's head.

51. The mask assembly of claim 47, wherein the top portion of the back portion includes a top strap dimensioned and configured to extend across a top of the patient's head from a first lateral side to a second lateral side of the patient's head.

52. The mask assembly of claim 47, wherein a thickness of each the upper straps and the lower straps is approximately 2 mm.

53. The mask assembly of claim 47, wherein the upper straps are arranged to be substantially parallel to each other.

54. The mark assembly of claim 47, wherein at least a portion of each of the lower straps are arranged to be substantially parallel to each other.

55. The mask assembly of claim 47, wherein each of the pair of upper straps and the pair of lower straps is formed of a composite having a first layer to be positioned against the patient's head, a second, middle layer constructed from foam, and a third layer including said loop portion.

56. The mask assembly of claim 47, further comprising vent holes adapted to vent exhaled air from the mask.

57. The mask assembly of claim 47, further comprising at least one port in communication with an interior of the mask.

58. The mask assembly of claim 47, further comprising an elbow connected to the frame, the elbow adapted to deliver pressurized gas to an interior of the mask.

59. The mask assembly of claim 47, wherein the mask is a full face mask.

60. The mask assembly of claim 47, wherein the mask is a nasal mask.

61. The headgear of claim 1, wherein the top portion and the pair of side portions form a generally triangular shape, the top portion or a base of the generally triangular shape being oriented for positioning towards or substantially at the crown of the head, while an apex of the generally triangular shape is dimensioned to lie generally above a point of contact between the patient's skull and muscles of the neck.

62. The headgear of claim 1, wherein the back portion is arranged to engage with an occiput of a patient's head.

63. The headgear of claim 18, wherein the opening of the back portion is adapted to receive an occiput of the patient's head.

64. The headgear of claim 33, wherein the back portion is arranged to engage with an occiput of a patient's head.

65. The mask assembly of claim 47, wherein the back portion is arranged to engage with an occiput of a patient's head.

66. The headgear of claim 1, wherein the downwardly angled portion of the headgear is formed without reinforcement or stiffeners.

67. The headgear of claim 18, wherein the downwardly angled portion of the headgear is formed without reinforcement or stiffeners.

68. The headgear of claim 33, wherein at least a portion of the headgear that extends behind the ears of the patient is formed without reinforcement or stiffeners.

69. The mask assembly of claim 47, wherein at least a portion of the headgear that extends behind the ears of the patient is formed without reinforcement or stiffeners.

70. The headgear of claim 1, wherein a lowest point of the back portion is dimensioned and shaped to engage the occiput region of the patient's head.

71. The headgear of claim 18, wherein a lowest point of the back portion is arranged to substantially avoid engagement with the sensitive area below the patient's occipital lobe.

72. The headgear of claim 33, wherein the back portion is structured and dimensioned to avoid engaging an area below an occipital lobe of the patient.

73. The mask assembly of claim 47, wherein the bottom portion of the back portion is dimensioned and configured so as to not engage with an area below an occipital lobe of the patient.

* * * * *